US006899877B2

(12) United States Patent
Peyman

(10) Patent No.: US 6,899,877 B2
(45) Date of Patent: May 31, 2005

(54) PROCESS FOR GENERATING PLASMIN IN THE VITREOUS OF THE EYE AND INDUCING SEPARATION OF THE POSTERIOR HYALOID FROM THE RETINA

(75) Inventor: Gholam A. Peyman, New Orleans, LA (US)

(73) Assignee: Minu, L.L.C., Pittsboro, NC (US)

( * ) Notice: Subject to any disclaimer, the term of this patent is extended or adjusted under 35 U.S.C. 154(b) by 215 days.

(21) Appl. No.: 10/227,546

(22) Filed: Aug. 26, 2002

(65) Prior Publication Data

US 2003/0113313 A1 Jun. 19, 2003

Related U.S. Application Data

(63) Continuation-in-part of application No. 09/978,684, filed on Oct. 18, 2001, now Pat. No. 6,585,972, which is a continuation-in-part of application No. 09/265,532, filed on Mar. 9, 1999, now Pat. No. 6,733,750.

(51) Int. Cl.$^7$ ......................... A61K 38/49; A61M 31/00
(52) U.S. Cl. ............................. 424/94.64; 424/94.63; 435/215; 435/216; 604/521; 604/522; 604/290; 604/294; 128/898
(58) Field of Search ............................. 424/94, 64, 63; 435/215, 216, 217; 604/521, 522, 290, 294; 128/898

(56) References Cited

U.S. PATENT DOCUMENTS 5,304,118 A * 4/1994 Trese et al. ................. 604/521
5,919,158 A * 7/1999 Saperstein et al. .......... 600/500
6,585,972 B2 * 7/2003 Peyman .................... 424/94.64
6,733,750 B1 * 5/2004 Peyman .................... 424/94.63

OTHER PUBLICATIONS

Hassan et al (Ophthalmology, 106(10): 1900–1907 (1999)).*
Guyton (Textbook of Medical Physiology, 6th Ed., W.B. Saunders Company, Philadelphia, 1981, pp. 98 and 99).*
Hesse et al (German J. Ophthalmol. 4:323–327 (1995)).*

* cited by examiner

Primary Examiner—Francisco Prats
(74) Attorney, Agent, or Firm—Roylance, Abrams, Berdo & Goodman, L.L.P.

(57) ABSTRACT

A process for inhibiting vascular proliferation separately introduces components into the eye to generate plasmin in the eye in amounts to induce complete posterior vitreous detachment where the vitreoretinal interface is devoid of cortical vitreous remnants. The process administers a combination of lysine-plasminogen, at least one recombinant plasminogen activator selected from the group consisting of urokinase, streptokinase, tissue plasminogen activator, chondroitinase, pro-urokinase, retavase, metaloproteinase, and thermolysin and a gaseous adjuvant to form a cavity in the vitreous. The composition is introduced into the vitreous in an amount effective to induce crosslinking of the vitreous and to induce substantially complete posterior vitreous detachment from the retina without causing inflammation of the retina. The gaseous adjuvant material is introduced into the vitreous simultaneously with or after the lysine-plasminogen and recombinant plasminogen activator such as recombinant urokinase to compress the vitreous against the retina while the composition induces the complete posterior vitreous detachment.

40 Claims, 1 Drawing Sheet

PROCESS FOR GENERATING PLASMIN IN THE VITREOUS OF THE EYE AND INDUCING SEPARATION OF THE POSTERIOR HYALOID FROM THE RETINA

CROSS-REFERENCE TO RELATED APPLICATION

This application is a continuation-in-part application of Ser. No. 09/978,684, filed Oct. 18, 2001, now U.S. Pat. No. 6,585,972, which is a continuation-in-part of Ser. No. 09/265,532 filed Mar. 9, 1999, now U.S. Pat. No. 6,733,750, and are hereby incorporated by reference in their entirety.

FIELD OF THE INVENTION

The present invention is directed to a process for inhibiting vascular proliferation in the retina by inducing posterior vitreous detachment in the eye of an animal. More, particularly invention relates to a process of generating plasmin in the vitreous of the eye in an amount to induce posterior vitreous detachment in the eye and to inhibit the effects of vitreous traction on the retina and other parts of the eye.

BACKGROUND OF THE INVENTION

Vitreous traction on the retina is caused by the attachment of vitreous fibrils to the basement membrane of the retina by cellular and molecular interactions between components of the vitreous and the inner limiting membrane. Fibronectin and laminin are extracellular glycoproteins which are known to be the most important components of the attaching mechanism for stabilizing the vitreoretinal attachment. The vitreous is a clear, proteinaceous material which fills the posterior of the eye between the lens and the retina. The vitreous is attached at its posterior face to the retina at the vitreoretinal junction along the inner limiting membrane. The vitreoretinal junction is a layer of basement membrane proximal to the vitreous.

The inner limiting membrane of the retina contains type I and type II collagen, laminin, fibronectin and glycoconjugates. These components have been found to bind collagen fibers between the vitreous and the inner limiting membrane.

Vitreous traction is recognized as a serious and potentially blinding complication in a number of vitreoretinal diseases following vitreoretinal surgery. An important aspect of most vitreoretinal surgery is to relieve the vitreous traction. Improvements have been made in mechanical vitrectomy techniques and instrumentation. However, the complete removal of the cortical vitreous from the retinal surface continues to be a difficult task. In some vitreoretinal proliferative disorders, surgical removal of the cortical vitreous can result in retinal break formation or bleeding from traction on retinal blood vessels.

Numerous studies have been conducted in attempts to develop a chemical system to separate the vitreoretinal interface without damage to the retina. These studies typically evaluate the vitreoretinal interface and have devised various pharmacological methods for inducing a traumatic separation between the vitreous and the retina. Intraoperative complications, such as retinal tears and hemorrhage can occur during surgical hyaloidectomy.

A number of enzymes and chemical substances have been used in attempts to induce posterior vitreous detachment. For example, chondroitinase did not show any activity but both hyaluronidase and Alpha-chymotrypsin caused posterior vitreous detachment. However, these enzymes produced peripapillary and vitreous hemorrhage in these eyes. Dispase, hyaluronidase, Alpha-chymotrypsin, collagenase, chondroitinase, and expansile gas are pharmacological agents used to induce PVD. The pharmacological agents have been used with limited results and have found to result in only partial or incomplete detachment. Dispase has been used in human and porcine cadaver eyes to separate the attachment of the posterior hyaloid from the inner limiting membrane. Dispase induced posterior vitreous detachment with minor morphologic changes in the inner retina. However, dispase, at low concentrations of 0.05–0.07 U, can cause proliferative vitreoretinopathy in 94% of cases up to 21 days after intravitreal injection. Doses equal to or higher than 0.05 U dispase can cause histologic epiretinal cellular membranes in all animals and 25% to 50% cataract formation which is related to dispase concentration. Some toxicity to the inner layer of the retina 15 minutes after injection of dispase has been reported, in spite of inducing posterior vitreous detachment. Intravitreal injection of hyaluronidase induced PVD in rabbits. The probable mechanism of inducing posterior vitreous detachment using hyaluronidase is vitreous liquefaction.

One study of a pharmacological method of inducing posterior vitreous detachment is described by Verstraeten et al., *Arch. Ophthalmol.*, Vol. 111, June 1993. This study evaluated the effectiveness of plasmin, which is a serine protease, in cleaning the vitreoretinal interface between the posterior vitreous cortex and the internal limiting membrane. The results showed some partial vitreous detachment and the presence of inflammatory cells. Other studies reported the application of plasmin in the vitreous in pediatric macular hole cases. A less traumatic separation of the vitreous from the retina and optic nerve head was induced by the injection of plasmin intravitreally immediately prior to vitrectomy. Plasmin and a plasminogen activator were evaluated for their effect on the basement membrane where plasmin was shown to be effective in degrading laminin and fibronectin which are found at the vitreoretinal junction and play an important role in vitreoretinal attachment. These processes that injected plasmin alone into the eye did not produce complete posterior vitreous detachment. Complete posterior vitreous detachment is attained only when combined with vitrectomy to mechanically remove the vitreous. Another example of a process of the use of plasmin in combination with a vitrectomy for removing the vitreous is disclosed in U.S. Pat. No. 5,304,118 to Trese et al.

Through various experiments, it has been found that plasmin alone does not result in complete posterior vitreous detachment and that the vitrectomy is necessary. Although not completely understood, it is believed that the plasmin may have some effect in loosening portions of the vitreous which enables the vitreous to be mechanically removed more easily than without the vitrectomy. Several studies, such as Verstraeten "Pharmacologic Induction of Posterior Vitreous Detachment in the Rabbit", Arc Opthalmol 1993; 111: 849–54, have shown that plasmin alone is not effective in inducing complete posterior vitreous detachment.

Another example of efforts to induce posterior vitreous detachment is disclosed in U.S. Pat. No. 5,722,428 to Kaplan et al. In this process dispase is selected to specifically cleave type IV collagen and fibronectin. The dispase is injected into the eye to promote posterior vitreous detachment. This process was shown to be ineffective in inducing complete vitreous detachment.

Accordingly, there is a continuing need for an effective process for inducing total or complete posterior vitreous detachment.

SUMMARY OF THE INVENTION

The present invention is directed to a composition and process for inhibiting the effects of vitreous contraction by inducing substantially complete posterior vitreous detachment in the eye without the need to remove the vitreous. More particularly, the invention is directed to a process of introducing a composition and a gaseous adjuvant into the eye to generate plasmin directly in the vitreous to induce complete posterior vitreous detachment and inhibit the effects of vitreous traction on the retina.

Accordingly, a primary aspect of the invention is to provide a process to produce plasmin in the eye and a process for selectively inducing complete posterior vitreous detachment that is efficient and effective to prevent or reduce the effects of vitreous contraction in the eye before the onset of complications from proliferative disorders. In one embodiment of the invention, the plasmin is generated in the vitreous and a gaseous material is introduced in the vitreous before retinal damage begins to occur in order to avoid the need to perform a vitrectomy.

Another aspect of the invention is to provide a composition and process for inducing crosslinking of the vitreous and for inducing substantially complete posterior vitreous detachment of the vitreous from the inner limiting membrane of the retina.

Still another aspect of the invention is to provide preventative or prophylactic processes by introducing a composition into the eye of a patient at risk of developing proliferative complications before the complications occur, where the composition includes plasminogen, a plasminogen activator and a gaseous adjuvant material to generate plasmin in the vitreous in non-toxic amounts.

A further aspect of the invention is to provide a process of inducing posterior vitreous detachment substantially without intraocular inflammation, electroretinography abnormalities or histologic abnormalities and without removal of the vitreous. In preferred embodiments, the plasminogen is recombinant lysine-plasminogen which is introduced in an amount of 100 $\mu$g or less, and preferably 75 $\mu$g or less. The plasminogen activator is preferably recombinant urokinase at a concentration of 200 IU/0.1 ml or less, preferably 100 IU/0.1 ml or less, and more preferably 50 IU/0.1 ml or less.

Another aspect of the invention is to provide a method and composition for crosslinking the vitreous and inducing posterior vitreous traction to separate the posterior hyaloid of the vitreous from the retina where the composition includes recombinant urokinase, recombinant lysine-plasminogen, a gaseous material and glucose.

A further aspect of the invention is to provide a composition and process for dissolving fibrin, fibronectin and blood clots in the vitreous of the eye.

Another aspect of the invention is to provide a method and composition for inhibiting retinal tears and hemorrhage by introducing a composition into the eye where the composition includes recombinant lysine-plasminogen, a recombinant plasminogen activator and an expanding gas without removing the vitreous from the eye.

A further aspect of the invention is to inject an expanding gas into the vitreous to compress the vitreous against the retina and injecting a composition into the eye to induce posterior vitreous detachment, where the composition comprises recombinant lysine-plasminogen, a recombinant plasminogen activator, and a collagen crosslinking agent.

The aspects of the invention are basically attained by providing a process for inhibiting vascular proliferation in the eye and preventing or inhibiting retinal hemorrhaging, retinal tears and retinal detachment in the eye of a patient caused by vitreous traction. The process comprises the steps of: introducing a composition into the vitreous of the eye of a patient in need thereof in an amount effective to induce posterior vitreous detachment to prevent or inhibit retinal hemorrhaging, retinal tears and retinal detachment. The composition comprises a pharmaceutically acceptable carrier, recombinant lysine-plasminogen and a recombinant plasminogen activator. An optional collagen crosslinking agent is introduced into the vitreous in an amount to induce crosslinking of collagen in the vitreous and to induce separation of posterior hyaloid from the inner limiting membrane in the eye. Each of the components of the composition is introduced into the eye in a non-toxic amount substantially without inflammation.

The aspects of the invention are further attained by providing a composition for inhibiting vascular proliferation comprising plasminogen and a plasminogen activator enzyme in an amount sufficient to convert the plasminogen to plasmin and a collagen crosslinking agent. The plasminogen and plasminogen activator are present in amounts to induce substantially complete posterior vitreous detachment from the retina without causing inflammation. The crosslinking agent is included in an amount sufficient to crosslink the collagen in the vitreous and separate the vitreous from the inner limiting membrane.

The aspects of the invention are also attained by providing a process for dissolving fibrin in the vitreous, comprising introducing a composition into the vitreous of the eye in an effective amount to dissolve blood clots present in the vitreous. The composition comprises a mixture of plasminogen, a plasminogen activator enzyme and an ophthalmologically acceptable carrier.

The aspects of the invention are further attained by providing a process for inhibiting vascular proliferation in the eye of a patient which comprises the step of introducing an effective amount of a composition into the vitreous of the eye for sufficient time to induce posterior vitreous detachment. The composition comprises plasminogen, a gaseous adjuvant and at least one active compound selected from the group consisting of urokinase, streptokinase, chondroitinase, tissue plasminogen activator, pro-urokinase, retavase, metaloproteinase, and thermolysin.

The aspects of the invention are still further attained by providing a process for preventing or inhibiting retinal hemorrhaging, retinal tears and retinal detachment in the eye caused by vitreous contraction. The process comprises the step of injecting a composition into the vitreous of the eye in an effective amount to induce posterior vitreous detachment in the eye. The composition comprises a pharmaceutically acceptable carrier, a collagen crosslinking agent, plasminogen and at least one active compound selected from the group consisting of urokinase, chondroitinase, pro-urokinase, tissue plasminogen activator, retavise, thermolysin, streptokinase, $\alpha$-thrombin, dipase, and transglutaminase.

The aspects of the invention are also attained by providing a composition for inducing posterior vitreous detachment in the eye of an animal and dissolving blood clots in the vitreous which comprises plasminogen, and a plasminogen activator enzyme in an amount sufficient to convert the plasminogen to plasmin where the plasminogen activator enzyme is selected from the group consisting of chondroitinase, pro-urokinase, tissue plasminogen activator, streptokinase, metaloproteinase, thermolysin, transglutaminase, and mixtures thereof. The plasminogen and plasminogen activator are present in amounts to induce posterior vitreous detachment from the retina without causing inflammation of the retina.

The aspects of the invention are still further attained by providing a process for dissolving fibrin in the vitreous of an eye comprising the steps of introducing a composition into the vitreous of the eye in an effective amount to dissolve fibrin present in the vitreous. The composition comprises a mixture of plasminogen, a plasminogen activator enzyme and an ophthalmologically acceptable carrier, and dissolving the fibrin in the vitreous.

Other aspects, advantages and salient features of the present invention will become apparent from the following detailed description, which, taken in conjunction with the annexed drawings, discloses preferred embodiments of the invention.

BRIEF DESCRIPTION OF THE DRAWING

Referring to the drawing which forms a part of this original disclosure in which:

The FIGURE is a cross-section of an eye showing a delivery device for introducing the composition to the eye.

DETAILED DESCRIPTION OF THE INVENTION

Figure 1:
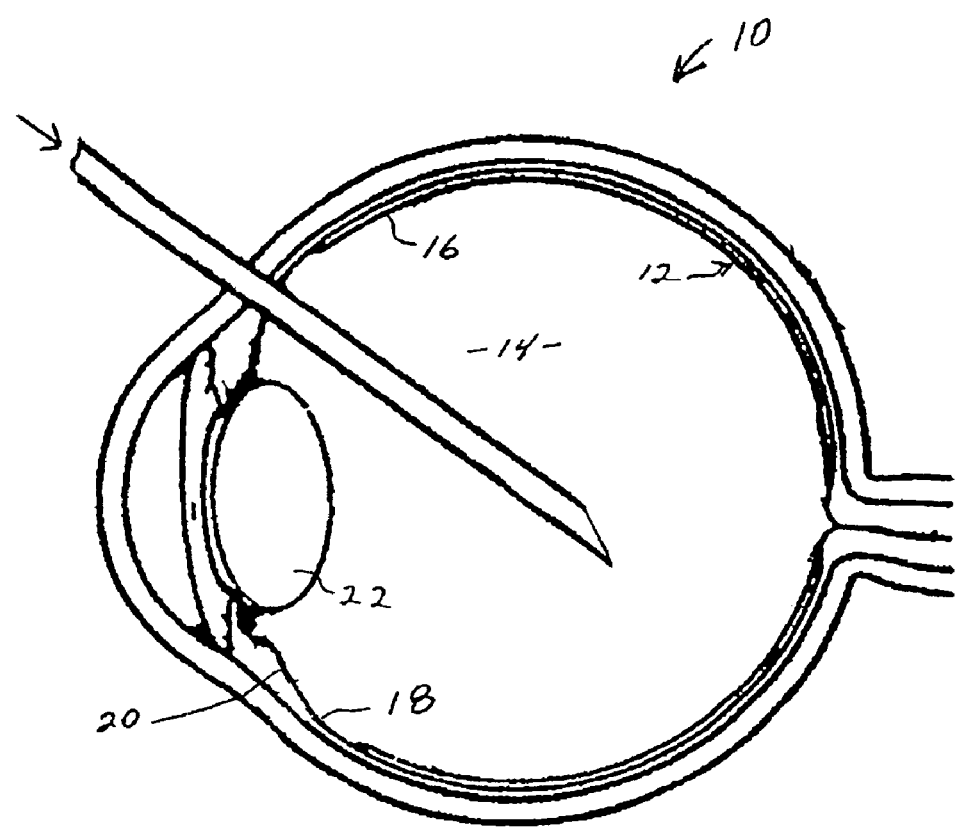

The present invention relates generally to a composition and process for treating the eye to inhibit or prevent the effects of vitreous traction on the retina without the need to remove the vitreous from the eye. More particularly, the invention is directed to a composition and process for inducing substantially complete posterior vitreous detachment in the eye of a patient before the proliferative stage without causing toxic effects on the retina. The invention is further directed to a composition and process for inducing crosslinking of the collagen in the vitreous and to induce separation of the posterior hyaloid from the inner limiting membrane of the eye.

The process of the invention is directed to the formation of plasmin in the vitreous in conjunction with the administration of an expanding gas or other gaseous adjuvant. It has been found that the separate intravitreal injection of recombinant lysine-plasminogen and a plasminogen activator, such as recombinant urokinase, results in a three-fold increase in plasmin concentration in the vitreous compared to injecting plasmin directly into vitreous or by premixing plasminogen and a plasminogen activator to produce plasmin before administering to the vitreous. Moreover, a greater incidence of complete posterior vitreous detachment occurs from the separate intravitreal injection in conjunction with a gaseous adjuvant.

It has been found that intravitreal plasmin injection alone may have some effect on the vitreous but does not produce complete separation of the vitreous from the posterior hyaloid and the retina. It is necessary to provide some form of mechanical assistance to separate the vitreous from the retina. A pars plana vitrectomy generates small oscillations in the vitreous which facilitates separation of the vitreoretinal attachments. Various studies have confirmed that administering plasmin alone into the vitreous does not result in complete separation of vitreous from the retina. Verstraeten, "Pharmacologic Induction of Posterior Vitreous Detachment in Rabbit", Arch. Ophthalmol. 1993; 111:849–54.

It has been found that intravitreal administration of a gaseous adjuvant in conjunction with the plasminogen and activator results in improved separation of the vitreous from the posterior hyaloid. An amount of the gaseous adjuvant is administered to compress the vitreous against the posterior hyaloid without damaging the retina. The gaseous adjuvant has been found to provide a synergistic effect when used in conjunction with the separate injection of recombinant lysine-plasminogen and recombinant urokinase.

As used herein, the term "substantially complete posterior vitreous detachment" and "substantially complete posterior vitreous separation" refers to separation of the vitreous from the inner limiting membrane to produce a clean vitreoretinal surface devoid of vitreous collagen and free of cortical vitreous remnants. As described in the Examples, the complete separation or detachment of the vitreous allows the vitreous to fall freely from the eye cup by gravity without the need for mechanical separation. The complete separation of the vitreous results in no vitreous strands remaining attached and a smooth surface of the inner limiting membrane (ILM) as determined by a scanning electron microscope (SEM). Incomplete or partial separation results in collagen fibers remaining attached to the retinal surface.

The degree of fibrovascular proliferation in some proliferative disorders is believed to be due, at least in part, to the effects of vitreous contraction and vitreous traction on the retina. Vitreous contraction is known to be related to the proliferative process in diabetic retinopathy, proliferative vitreoretinopathy, central vein occlusion, branch retinal vein occlusion and macular hole. Vitreous adhesion to the retina may play an important role in the progression of diabetic retinopathy to the proliferative stage.

The present invention is directed to a process of preventing or inhibiting the onset of various disorders that are the result of vitreous adhesion to the retina and vitreous contraction without performing a vitrectomy. A vitrectomy can cause damage to the retina so that it is desirable to avoid performing a vitrectomy while being able to prevent the effects of vitreous traction. The process of the invention is able to prevent or inhibit the disorders in the eye caused by attachment of the vitreous to the retina without removing the vitreous from the eye. In particular, the invention is directed to a process of treating a patient at risk of developing proliferation disorders, such as a diabetic patient, by inducing complete posterior vitreous detachment as a prophylactic step in preventing or delaying the onset of disorders associated with vitreous contraction. In one embodiment of the invention, the composition is introduced into the eye of a diabetic patient to inhibit progression of diabetic retinopathy. Preferably, the composition is introduced into the eye before the proliferative disorders occur. The composition can remain in the eye for extended periods of time without causing inflammation, thereby avoiding the need to perform a vitrectomy. In one embodiment, the composition is introduced into the vitreous of the eye before the onset of proliferative disorders and is allowed to remain in the eye indefinitely without removing the vitreous or the composition from the eye.

In further embodiments, the invention is directed to a process for inhibiting complications in central and branch retinal vein occlusion, such as retinal neovascularization and macular edema by inducing posterior vitreous detachment in a patient in need of such treatment. A further aspect is to provide a process for treating idiopathic impending or full-thickness macular hole by inducing posterior vitreous detachment. Preventing or reducing the incidence of retinal detachment, retinal tears and retinal hemorrhage caused by vitreous contraction can be achieved by inducing substantially complete posterior vitreous detachment before such disorders occur and without removing the vitreous from the eye.

Posterior vitreous detachment is induced in the eye of an animal by introducing the compounds at non-toxic levels into the vitreous of the eye that are able to generate plasmin directly in the vitreous. The compounds can be introduced alone or in combination. In preferred embodiments, the compounds are injected separately to generate the plasmin in the vitreous and preferably at the point of attachment of the vitreous to the retina. The present invention is based on the discovery that the compounds when used alone are not effective in inducing posterior vitreous detachment or are able to induce posterior vitreous detachment only at toxic levels that cause inflammation. In preferred embodiments of the invention, compounds are administered separately and are used in combination, with each compound being present in a non-toxic dose so that the combination of compounds produce plasmin that is able to induce substantially complete posterior vitreous detachment to inhibit the progression of vascular proliferation. The non-toxic dosages can remain in the eye indefinitely without causing inflammation or other adverse effects in the eye. As used herein, the term "non-toxic" amount refers to an amount that does not cause inflammation, retinal vascular constriction or hemorrhages in the eye and particularly does not cause inflammation of the retina and does not produce any changes in the eye as determined by electroretinogram and histology studies. The non-toxic amounts can remain in the eye indefinitely without requiring the compounds or the vitreous to be removed.

The amount of the active compound or compounds introduced into the eye determines the extent of posterior vitreous detachment and the rate of detachment. In one embodiment, a single dose can be introduced into the vitreous to produce a rapid detachment. In further embodiments, a series of small dosages is introduced over a period of time to induce a slower and controlled rate of detachment.

In one preferred embodiment of the invention, a combination of recombinant lysine-plasminogen and a recombinant plasminogen activating enzyme are separately injected into the vitreous in non-toxic and effective amounts to generate plasmin at the point of vitreous attachment to induce posterior vitreous detachment. Preferably, a gaseous adjuvant is injected into the vitreous before, after or simultaneously with the recombinant lysine-plasminogen and the recombinant plasminogen activating enzyme. In one embodiment, the composition includes the combination of recombinant lysine-plasminogen, recombinant urokinase, a gaseous material and an optional collagen crosslinking agent. A particularly preferred embodiment introduces a composition into the vitreous of the eye, where the composition contains recombinant lysine-plasminogen, recombinant urokinase as the plasminogen activator and glucose as a collagen crosslinking agent in a balanced aqueous saline solution. In further embodiments, plasminogen and the activator can be used alone or in combination with another compound capable of inducing posterior vitreous detachment. Examples of compounds that can be used in combination with the recombinant plasminogen, recombinant urokinase and the gaseous adjuvant include streptokinase, metaloproteinase, hyaluronidase, chondroitinase (chondroitinase ABC or AC), dipase, α-thrombin, transglutaminase, pro-urokinase, retavase, thermolysin and tissue plasminogen activator (TPA). These compounds are generally used in amounts ranging from about 500 IU to about 2500 IU depending on the particular compound and the toxicity level of the compound and the desired rate and extent of detachment.

In one embodiment of the invention, a collagen crosslinking agent is introduced into the vitreous in combination with plasminogen, plasminogen activator and a gaseous material. Preferably, the plasminogen is recombinant lysine-plasminogen and the urokinase is recombinant urokinase to provide substantially pure forms of the compounds with reduced risk of transmission of viruses and other undesirable contaminants. The collagen crosslinking agent is introduced into the vitreous in an amount effective to induce crosslinking of the collagen in the vitreous. The vitreous normally contains collagen which is understood to form the posterior hyaloid. The posterior hyaloid is attached to the inner limiting membrane of the retina by fibrils from the vitreous.

The recombinant lysine-plasminogen of the invention is the truncated form of natural plasminogen with a terminal lysine group. The present invention includes the discovery that recombinant lysine-plasminogen is more readily activated to plasmin in the vitreous than human plasminogen. The recombinant lysine-plasminogen enables the rate of production and the amount of plasmin to be more readily controlled and predicted. The higher rate of conversion of recombinant lysine-plasminogen to plasmin produces a maximum concentration of plasmin in the vitreous in a short period of time thereby providing an effective concentration of plasmin to induce the posterior vitreous detachment.

Plasminogen is secreted by the liver as a single chain 92-kD glycoprotein consisting of 791 amino acid residues with Glu as the N-terminal amino acid. The molecule is composed of five kringle-like domains having lysine binding sites and C-terminal domain homologous to other trypsin-like proteases. The kringle domains mediate interactions of plasminogen and plasmin with substrates, inhibitors, and cell membranes, which are crucial for the activation of plasminogen and localization of proteolytic activity of plasmin.

The plasminogen molecule contains amino acids, 24 disulfide bridges, no free sulfhydryls and 5 regions of internal sequence homologous (kringles) between Lys 77 and Arg 560. Plasminogen contains one high and four low affinity binding sites. The high affinity binding site is within the first kringle region of plasminogen. Native Glu-plasminogen can be cleaved by plasmin at peptide bonds between Arg 67-Met 68, Lys 76-Lys 77 or Lys 77-Val 78 with the release of an 8 kD N-terminal polypeptide and the formation of Lys-plasminogen. Native Glu-plasminogen has a molecular weight of 88,000 daltons while Lys-plasminogen has a molecular weight of 83,000 daltons. Splitting of the Arg 561 -Val 562 peptide bond converts the plasminogen to the active enzyme plasmin consisting of two polypeptide chains linked by a disulfide bond. The N-terminal heavy A-chain possesses all of the kringle domains. The C-terminal light B-chain contains the catalytic site composed of His 602, Asp 645 and Ser 740.

The combination of recombinant lysine-plasminogen and recombinant urokinase when introduced into the vitreous of the eye reacts to produce plasmin. After the Lys-plasminogen and recombinant urokinase are administered intravitreally, a gaseous adjuvant is injected into the vitreous, which in combination with the generated plasmin is able to induce substantially complete posterior vitreous detachment. By introducing the compounds separately into the eye, the plasmin is produced in situ and delivers the plasmin at a continuous rate for a sustained period of time. It has been discovered that the separate injection of Lys-plasminogen and recombinant urokinase followed by injection of a gaseous adjuvant results in a three fold increase in the plasmin concentration in the vitreous compared to pre-mixing the compounds or injecting plasmin directly. Producing the plasmin over a period of time supplies the tissue in the eye with a continuous supply of the plasmin and maintains a more constant and predictable concentration of the plasmin to achieve separation without inflammation of the retina or other tissue in the eye. It has been found that plasmin is unstable and when produced before introducing into the eye is depleted very quickly and produces inconsistent results. Test results have shown that injecting human plasmin alone in the eye does not result in complete detachment of the vitreous from the retina. In addition, because plasmin is unstable, a large dose must be introduced into the eye at one time. When the initial concentration of the plasmin is very high, the high concentration results in inflammation and other undesirable effects in the eye so that the plasmin and the vitreous must be removed. The plasmin is quickly depleted so that complete separation of the posterior hyaloid from the retina is difficult, unpredictable, and usually results in only partial separation of the vitreous from the retina when introduced directly into the eye. By introducing a mixture of recombinant lys-plasminogen and a recombinant plasminogen activator into the eye, effective non-toxic dosages of plasmin can be produced for a sustained level to induce posterior vitreous detachment in a controlled and predictable manner. In addition, the non-toxic dosage can remain in the eye without causing inflammation so that a vitrectomy is not required.

In a preferred embodiment, the recombinant lysine-plasminogen and recombinant activator are delivered in combination with an amount of sterile gaseous adjuvant, such as air or an expanding gas. Preferably, gaseous material is injected into the posterior chamber of the eye. In one embodiment, the air or expanding gas is injected into the vitreous in the posterior chamber and immediately thereafter administering the composition to induce posterior vitreous detachment. In other embodiments, the gaseous adjuvant is introduced simultaneously with or after the introduction of the composition for inducing posterior vitreous detachment.

The gaseous adjuvant can be air, an expanding gas or liquefiable gas, or mixtures thereof, that is non-toxic to the eye. Examples of suitable gaseous materials include $SF_6$ (sulfur hexafluoride) and perfluorocarbons, such as $C_2F_6$ (hexafluoroethane), $C_3F_8$ (octafluoropropane), and $C_4F_8$ (octafluorocyclobutane). Other suitable gases include oxygen, nitrogen, carbon dioxide, argon, and other inert gases. The volume of the gaseous material that is introduced into the eye can vary depending on the gaseous material, the patient, and the desired result. For example, the volume of air that is injected into the posterior chamber can range from about 0.5 ml to about 0.9 ml. Other gaseous materials, such as $SF_6$ and perfluorocarbon gases can range from about 0.3 ml to 0.5 ml. Preferably, the gaseous material is introduced into the posterior chamber of the eye in an amount sufficient to compress the vitreous against the posterior hyaloid and form a cavity in the vitreous without damaging the eye. In preferred embodiments, the gaseous adjuvant is introduced into the vitreous to form a cavity that fills about 40% to about 60% of the internal volume of the intraocular cavity.

In a preferred embodiment, the gaseous material is injected into the posterior chamber of the eye without removing the vitreous and is allowed to remain in the vitreous indefinitely. The gaseous material is injected in an amount to compress or position the retina against the choroid and to compress the vitreous against the retina. Thereafter, the composition containing a mixture of recombinant lys-plasminogen, a plasminogen activator, and an optional collagen crosslinking agent is injected into the vitreous. The gaseous material forms a bubble within the vitreous to compress the vitreous against the posterior region and enables the composition to separate the vitreous from the posterior hyaloid without damaging the retina. In one embodiment, the gaseous material is a mixture of air and a perfluorocarbon gas in proportions to produce an expanding gas mixture. The amount of the gaseous material introduced into the eye is preferably an amount sufficient to increase the internal volume of the eye and compress the vitreous against the retina without causing damage to the retina, choroid, or other parts of the eye.

In some embodiments of the invention, a liquid perfluorocarbon having a low vapor pressure is injected into the vitreous of the eye. The perfluorocarbon can be injected in liquid form at ambient temperature and is heated to body temperature. As the perfluorocarbon is heated, it changes to the gaseous phase. In still further embodiments, a gaseous perfluorocarbon can be dissolved in a liquid perfluorocarbon and injected into the eye in an amount to release the gaseous perfluorocarbon to the vitreous. Examples of perfluorocarbons include perfluoro-n-pentane, perfluoro-n-hexane, perfluoro-n-heptane and perfluoromethyl-cyclopentane.

The gaseous material is injected into the eye and allowed to remain indefinitely. The gaseous material remains in the eye for several days and is gradually absorbed by the body. The rate of absorption of the gaseous material depends on the particular gas. Most perfluorocarbons are absorbed in about 3 to 10 days. Air, nitrogen and some other gases typically require a slightly longer period of time to be absorbed compared to perfluorocarbon gases. Where it is desirable, the vitreous can be removed after the gaseous material is absorbed and the composition has caused the posterior vitreous detachment. In a preferred embodiment, the vitreous is allowed to remain in the eye for an extended period of time, or indefinitely without inflammation. In this embodiment, the combination of an expanding gas, plasminogen and plasminogen activator are introduced into the eye as a prophylactic step before the onset of proliferative disorders and without removing the vitreous from the eye.

The collagen crosslinking agent can be introduced into the vitreous of the eye in an amount to cause crosslinking, which causes the vitreous to gel and shrink slightly and pull away from the inner limiting membrane and the retina. Preferably, the composition contains generally about 3 wt % to about 6 wt %, and preferably about 5 wt % of a collagen crosslinking agent. It has been found that the collagen crosslinking agent in combination with plasminogen and a plasminogen activator can effectively induce posterior vitreous detachment of the posterior hyaloid of the vitreous from the inner limiting membrane and the retina while causing the vitreous to shrink slightly and detach from the retina without causing damage to the retina. The collagen crosslinking agent causes the vitreous to gel and become stiffer and less fluid. After subjecting the vitreous to a crosslinking agent, the vitreous can be removed from the eye, if desired, using a vitrectomy device without damage to the retina. The vitreous is replaced with a suitable stable solution as in a conventional vitrectomy. In other embodiments, the vitreous is not removed but is left in the eye.

The crosslinking agent is preferably dispersed in a pharmaceutically acceptable carrier, such as a 5 wt % or balanced saline solution. The crosslinking agent can be selected from a number of compounds capable of inducing crosslinking of collagen in the vitreous at non-toxic dosages. In one embodiment, the crosslinking agent is transglutaminase. In another embodiment, the collagen crosslinking agent is a reducing sugar. Examples of suitable reducing sugars are selected from the group consisting of fructose, glucose, glycerose, threose, erythose, lyxose, xylose, arabinose, ribose, allose, altrose, mannose, fucose, gulose, idose, galactose, and talose. In further embodiments, the reducing sugar can be any suitable diose, triose, tetrose, pentose, hexose, septose, octose, nanose or decose.

In alternative embodiments, the collagen crosslinking agent can contain a metal cation capable of inducing crosslinking of collagen. Examples of suitable crosslinking agents include sodium persulfate, sodium thiosulfate, ferrous chloride, tetrahydrate or sodium bisulfite. The metal cations are generally selected from the group consisting of sodium, potassium, magnesium, and calcium. The metal cations are typically salts of metal chlorides, bromides, iodides, phosphates, sulfates and acetates.

The process of the invention dissolves fibrin and blood clots in the vitreous and induces posterior vitreous detachment by introducing a composition into the vitreous of the eye in an effective amount to induce complete or substantially complete posterior vitreous detachment. The composition in one embodiment includes plasminogen and a plasminogen activator for converting the plasminogen to plasmin and stimulating the release of plasmin in the eye. A preferred activator is urokinase although other enzymes such as streptokinase can be used. Although the mechanism for inducing posterior vitreous detachment is not completely understood, the plasminogen and activator have been found to produce cleavage at the vitreoretinal interface between the posterior vitreous cortex and the inner limiting membrane.

The composition preferably contains a nontoxic amount of one or more active compounds in a pharmaceutically acceptable carrier. It has been discovered that plasminogen in combination with urokinase and a gaseous adjuvant can be introduced into the vitreous at a dose such that substantially complete posterior vitreous detachment occurs without inflammation, retinal vascular constriction or hemorrhages, and without ERG or histologic abnormalities. The dosages herein are expressed in terms of international units (IU) and caseinolytic units (CU). The lys-plasminogen dispersed in an ophthalmologically suitable carrier is generally introduced into the vitreous of the eye at a dose of about 0.01 CU to about 16.0 CU. The lys-plasminogen is generally introduced at a dose of about 2.0 CU or less and usually at a dose of at least about 0.1 CU to produce complete posterior vitreous detachment when used in combination with the plasminogen activator and the gaseous adjuvant. It has been found that prolonged exposure at dosages of plasminogen greater than 2.0 CU can cause inflammation of the retina, while a dosage of less than 0.1 CU of lys-plasminogen is only partially effective in inducing complete posterior vitreous detachment within a 12 hour period. In other embodiments, the lys-plasminogen is introduced at a dosage of about 500 IU to about 1000 IU. In one embodiment, the lys-plasminogen is introduced into the vitreous in an amount of 1000 IU or less. Preferably, the lys-plasminogen is administered at concentrations of less than 250 µg/0.1 ml. Typically, the lys-plasminogen is administered in a pharmaceutically acceptable carrier at a concentration of about 50 µg/0.1 ml, and preferably about 100 µg/0.1 ml or less.

The amount of the active compounds introduced into the vitreous can vary depending on various factors. Low levels of the active compounds can be used to induce a slow rate of posterior vitreous detachment where the active compounds remain in the eye for long periods of time. Alternatively, high doses of the active compounds can be used to induce a rapid posterior vitreous detachment. For example, plasminogen at doses of 4 CU and 6 CU can be introduced into the vitreous which induce posterior vitreous detachment in several hours. At higher doses of plasminogen greater than about 2 CU, the plasminogen can cause inflammation of the retina. Therefore, at higher dosages, it is generally preferred to introduce the plasminogen composition for sufficient time to induce the desired extent of posterior vitreous detachment and then remove the vitreous and/or the plasminogen composition from the eye to prevent or minimize inflammation of the retina or other abnormalities. Standard vitrectomy surgical techniques can be used to remove the vitreous from the eye and replace the vitreous with, an ophthalmologically acceptable solution or composition to stabilize the ocular cavity. In other embodiments, the composition is left in the eye without performing the vitrectomy.

The plasminogen activator is an enzyme capable of stimulating the conversion of plasminogen to plasmin in the eye. The activator is preferably an enzyme that is capable of dissolving blood clots. The preferred enzyme is recombinant urokinase, although other enzymes, such as streptokinase and human tissue plasminogen activator (TPA), can be used. In a preferred embodiment, the plasminogen activator is introduced into the eye at a dosage of about 1000 IU or less, and typically about 200 IU to 1000 IU.

Urokinase can be included to provide a dose of at least about 500 IU and less than about 2500 IU. In preferred embodiments, the composition contains about 1,000 IU or less since this dosage has been found effective in converting the plasminogen to plasmin in the eye and is effective in inducing posterior vitreous detachment without causing inflammation. In addition, it has been found that a dosage of 1000 IU or less can remain in the eye without causing inflammation and without requiring the vitreous to be removed. It has been found that a dose of 5,000 IU or more can cause inflammation of the retina. The higher doses of the enzyme activator can activate the plasminogen normally present in the tissue. Tissue plasminogen activator (TPA) is used at a dose of about 25 micrograms or less. It has been found that tissue plasminogen activator used at dosages greater than 25 micrograms can be toxic in the eye. Streptokinase is typically used at dosages similar to the dosages for urokinase. In one embodiment the composition contains about 1000 IU plasminogen and about 200 IU urokinase.

Previous studies of the vitreoretinal junction and the inner limiting membrane of the retina demonstrated that vitreous fibrils are attached to the basement membrane of the retina by cellular and molecular interactions between the various components of the vitreous and the inner limiting membrane. The attachment of the vitreous to the inner limiting membrane is primarily by fibronectin and laminin.

The inner limiting membrane contains type I and IV collagen, laminin, fibronectin and glycoconjugates that bind collagen fibers between the vitreous and the inner limiting membrane. Immunofluorescent studies have demonstrated the presence of fibronectin in the vitreous cortex and the inner limiting member. However, laminin is found only in the basement membrane components of the inner limiting membrane and associated with type IV collagen. Immunofluorescence studies further show that the laminin and fibronectin are found along the periphery of the retina and the ora serrata. These bands are generally thicker in the posterior retina, especially in younger people. The size of the bands shows a direct correlation to the age of the person.

The effect of plasmin on glycoprotein and the collagenous component of basement membrane has been studied. Plasmin may play a role in removing the glycoprotein components of the basement membrane including the fibronectin and laminin. Plasmin can expose the type IV collagen to degradation by different enzymes such as collagenase and elastase, but cannot by itself degrade the collagenous component of the basement membrane. Proteolysis of the laminin and the fibronectin found in the vitreous and on the retinal surface may play a very important role in inducing posterior vitreous detachment.

Urokinase is a serine protease which has been suggested to play a role independent of plasminogen effects. Previous efforts have shown that urokinase failed to produce significant degradation of fibronectin or other basement membrane components. In vitro studies revealed that urokinase may have some effects on the cell membrane associated fibronectin-binding site.

Some studies of posterior vitreous detachment found no correlation between fibronectin and laminin distribution and the occurrence of posterior vitreous detachment. Posterior vitreous detachment is not simply a thickening of the inner limiting membrane, but rather a complex phenomenon. Plasmin may facilitate the formation of posterior vitreous detachment by the proteolysis of laminin and fibronectin. Plasmin has some additional secondary effects against attachment of the vitreoretinal interface. Plasmin has an indirect activating effect on collagenase and may trigger release of elastase, which digests type IV collagen. Elastase is released from the PMNL which induces an inflammatory process. The use of plasmin alone in prior studies was shown to produce reversible ERG depression by the third day after injection due to hyperosmolarity of plasmin solution and also cause inflammation in the eye.

The process of the invention utilizes the combination of plasminogen and an enzyme for activating plasminogen and a gaseous adjuvant. The plasminogen activator is preferably recombinant urokinase or streptokinase. The enzymes are found to have a synergistic effect when combined with plasminogen and introduced into the eye since plasmin alone and enzyme alone are not able to induce complete posterior vitreous detachment, and can cause inflammation of the retina at high doses.

Plasmin is unstable and must be utilized rapidly to minimize converting to an inactive form. When plasmin is introduced directly into the vitreous, the plasmin is depleted quickly and can be depleted before complete posterior vitreous detachment occurs. In preferred embodiments of the invention, the plasminogen and the plasminogen activator enzyme are each dispersed in a suitable ophthalmic carrier and injected separately into the vitreous of the eye where the plasmin is generated in the vitreous. The composition containing both the plasminogen and the plasminogen activator will produce plasmin in situ.

Plasmin is produced in situ in the eye by the reaction between the plasminogen and the activator composition, as well as the reaction between the tissue plasminogen and the activator. It has been found that by introducing plasminogen, a plasminogen activator and the gaseous adjuvant into the vitreous, plasmin is continuously produced over a period of time to maintain a threshold plasmin concentration in the vitreous for sufficient time to attain complete vitreous detachment. In one embodiment of the invention, the plasminogen and the plasminogen activator are delivered to the vitreous of the eye simultaneously through separate delivery devices or sequentially through separate delivery devices in amounts sufficient to produce plasmin for a period of time in amounts to induce substantially complete posterior detachment. Typically, the delivery device is a syringe suitable for injecting materials into the eye.

In one embodiment, the plasminogen and the plasminogen activator are introduced into the eye through separate needles so that the components are distributed in the vitreous and can be targeted at interface between the posterior hyaloid and the retina. In this manner, the plasminogen and the activator react as the components come into contact with each other to produce plasmin over a period of time. This provides a sustained level of plasmin in the eye for a period of time without producing toxic levels in the eye.

In further embodiments of the invention, plasminogen is used in combination with a non-toxic amount of a chondroitinase, metaloproteinase or hyaluronidase. Each of the compounds are used in non-toxic amounts. By using a combination of active compounds, an effective total concentration can be obtained for inducing posterior vitreous detachment where the concentration of each component is below a toxic threshold level. In further embodiments, plasminogen or plasmin can be used in combination with α-thrombin, pro-urokinase, transglutaminase, retavase, thermolysin, TPA, either alone or in combination in a non-toxic amount.

The FIGURE illustrates an embodiment of the invention showing an eye 10, retina 12 and vitreous humor 14. The strongest adhesion between the vitreous 14 and the retina 12 occurs at the vitreous base 16. The vitreous base 16 is associated with the ora serrata 18 and the pars plana 20. The vitreous 14 is also attached at the peripheral central retina and at the posterior of the lens 22. The attachment at these locations is generally less than at the ora serrata 18 and the pars plana 20. Strong adhesion areas are also found around the optic nerve head and macula. As shown in the FIGURE, a delivery device, such as a needle, is inserted into the vitreous and the composition is introduced through a delivery device.

Generally, the composition is injected to the center of the vitreous although the composition can be introduced to other areas. In one embodiment, two separate needles can be positioned to deliver the components at the posterior region of the eye so that the plasmin is generated at the posterior region. The composition can be administered intravitreal, subvitreal, sublenticular, and in the posterior chamber of the eye.

In embodiments of the invention, the composition of the invention, which includes recombinant lys-plasminogen, a recombinant plasminogen activator and gaseous material, are introduced into the vitreous humor of the eye. The composition can be introduced as a preventative step before the onset of proliferative disorders without removing the vitreous from the eye. In other embodiments, the composition can be introduced prior to or in combination with intraocular surgery to induce posterior vitreous detachment prior to surgery. Examples of surgical procedures where posterior vitreous detachment is induced include vitrectomy for macular hole surgery, vitrectomy for diabetic retinopathy and other proliferative vascular retinopathies, repair and prevention of retinal detachment, subretinal surgery submacular surgery and retinal transplantation. The inducement of posterior vitreous detachment can also be used to treat blinding complications such as diabetic retinopathy, central vein occlusion, proliferative vitreoretinopathy and proliferative vascular retinopathy before these disorders occur.

The compound or combination of compounds are suspended or dispersed in a suitable carrier for introducing into the eye of a subject. Suitable carriers are nontoxic to the eye or the subject and do not inhibit the detachment of the vitreous from the retina. The carrier can include various salts, buffering agents, preservatives, compatible carriers and other therapeutic components such as steroids, antibiotics and anti-inflammatory agents as known in the art. An example of a suitable anti-inflammatory agent is dexamethazone. Preferably, the carrier is a sterile liquid having a pH and osmolarity that are compatible with the normal vitreous. Suitable carriers include balanced salt solution, phosphate buffered saline lactated Ringer's solution and the like as known in the art. The resulting suspension generally contains, for example, about 0.1 CU to about 25 CU per ml of plasminogen and typically about 500 IU to 1000 IU plasminogen.

Various antibiotics can be used in conjunction with the compounds. Suitable antibiotics include amikacin, clindamycine, cefazoline, gentamicin, vancomycin, and mimocycline and derivatives thereof such as minocin, climomycin, minomycin and vetrin. Amikacin is typically injected into the vitreous at a dose of about 200 micrograms. Dexamethasone, clinomycin and vancomycin are typically used in amounts of about 500 micrograms.

A composition of recombinant lys-plasminogen, a recombinant plasminogen activator enzyme and a gaseous adjuvant can also be used in combination with other enzymes or agents which do not induce complete posterior vitreous detachment when used alone. For example, the composition can be used in conjunction with enzymes, such as at least one selected from the group consisting of a chondroitinase (chondroitinase ABC or AC), dispase and, α-thrombin and transglutaminase. It is believed that these compounds have a synergistic effect when used simultaneously with the combination of plasminogen alone and with a mixture of plasminogen and a plasminogen activator enzyme.

The compounds are introduced into the eye in amounts to induce complete or substantially complete posterior vitreous detachment without causing inflammation of the retina or other adverse side effects. The suspension or dispersion is typically injected into the eye in an amount of about 0.1–0.5 ml. The amounts of the respective components can vary depending on the condition being treated, the pH and condition of the vitreous and the time requirements for attaining vitreous detachment. The volume of the eye and the age of the subject are also factors in determining the amount of components introduced. In further embodiments of the invention, the composition can be introduced into the eye in an amount sufficient to attain a desired degree of vitreous detachment which may be less than complete detachment.

In a preferred embodiment, the recombinant lysine-plasminogen and recombinant activator are delivered in combination with an amount of sterile gaseous adjuvant, such as air or an expanding gas. Preferably, gaseous material is injected into the posterior chamber of the eye. In one embodiment, the air or expanding gas is injected into the vitreous in the posterior chamber and immediately thereafter administering the composition to induce posterior vitreous detachment. In other embodiments, the gaseous adjuvant is introduced simultaneously with or after the introduction of the composition for inducing posterior vitreous detachment.

The gaseous adjuvant can be air, an expanding gas or liquefiable gas, or mixtures thereof, that is non-toxic to the eye. Examples of suitable gaseous materials include $SF_6$ (sulfur hexafluoride) and perfluorocarbons, such as $C_2F_6$ (hexafluoroethane), $C_3F_8$ (octafluoropropane), and $C_4F_8$ (octafluorocyclobutane). Other suitable gases include oxygen, nitrogen, carbon dioxide, argon, and other inert gases. The volume of the gaseous material that is introduced into the eye can vary depending on the gaseous material, the patient, and the desired result. For example, the volume of air that is injected into the posterior chamber can range from about 0.5 ml to about 0.9 ml. Other gaseous materials, such as $SF_6$ and perfluorocarbon gases can range from about 0.3 ml to 0.5 ml. Preferably, the gaseous material is introduced into the posterior chamber of the eye in an amount sufficient to compress the vitreous against the posterior hyaloid and form a cavity in the vitreous without damaging the eye. In preferred embodiments, the gaseous adjuvant is introduced into the vitreous to form a cavity that fills about 40% to about 60% of the internal volume of the intraocular cavity.

EXAMPLES

In the following examples, one eye each of 78 New Zealand white rabbits was used in this study. Animals were treated in accordance with the Association for Research in Vision and Ophthalmology (ARVO) Resolution on the Use of Animals in Research. All procedures were done under general anesthesia. The animals were anesthetized with an intramuscular injection of ketamine hydrochloride (35 mg/kg) and xylazine hydrochloride (5 mg/kg). Pupillary dilation was achieved with phenylephrine hydrochloride 2.5%, tropicamide 1%, and cyclopentolate 1%.

The r-lys-plg was obtained from Novo Nordisk (Maaloev, Denmark) as a lyophilized powder and was kept at −80° C. until reconstitution. Endotoxin-free sterile water ($H_2O$) was used for reconstitution of the r-lys-plg unless otherwise stated.

R-UK, provided by Abbott Laboratories (Abbott Park, Ill., USA), in the form of a lyophilized powder and kept at 4° C. until it was reconstituted with endotoxin-free sterile $H_2O$, unless otherwise stated.

Example 1

In this Example, the concentration of plasmin was determined in various test samples. All enzyme assays were performed at 25° C. in 0.05 M Tris-HCl buffer (pH 7.4, containing 0.038 M NaCl and 0.01% Tween 80) or in lysine-phosphate buffer (pH 7.5, 0.1 M phosphate buffer, 0.07 M lysine) in a total volume of 1 ml. Chromogenic plasmin substrate S-2251 (H-D-Val-Leu-Lys-pNA≅2 HCl, DiaPharma, Columbus, Ohio) at a final concentration of 0.6 mM was used to measure plasmin generation. Absorbance was monitored continuously at 405 nm using the UV-1601spectrophotometer (Shimadzu Scientific Instruments, Inc., Columbia, Md.) over a period of 5 minutes. All measurements were performed in duplicate and the mean values were used as the test result.

The ability of S-2251 to be cleaved to a colored product was tested using purified human plasmin (Sigma-Aldrich, St. Louis, Mo.). The activities of r-UK and r-lys-plg were separately tested with purified human plasminogen (Sigma-Aldrich) and human urokinase (American Diagnostica Inc., Greenwich, Conn.), respectively, using S-2251.

The standard plasmin concentration curve was prepared using eight different concentrations of purified plasmin from human plasma (Sigma-Aldrich). The plasmin concentrations in mixtures of r-lys-plg and r-UK and in vitreous samples were calculated by using the standard plasmin concentration curve and its formula:

[Plasmin] u/l=5000×$V$(total measuring volume)/$v$(vitreous sample volume)×ΔA/sec.

The absolute concentrations of plasmin were determined using the following formula provided by the manufacturer of the S-2251 substrate:

[Plasmin] u/l=6240×V(total volume)/v(sample volume)×ΔA/sec.

The results using both formulas were compared.

Varying concentrations of r-UK and 50 μg/ml r-lys-plg were reconstituted and mixed in Tris-HCl buffer (pH 7.4, containing 0.038 M NaCl and 0.01% Tween 80) at 25° C. The plasmin concentrations of these solutions were tested at different time points after mixing to determine the optimal incubation time and optimal relative concentrations of reagents under the conditions described.

To determine the correct quantity of reagents to be injected, the amounts of r-lys-plg and r-UK in the test volume of 1 ml were multiplied by 1.5 to achieve the same concentrations in the larger volume (approximately 1.5 ml) of rabbit vitreous.

Solutions of r-lys-plg and r-UK were prepared for separate administration to the vitreous. R-lys-plg and r-UK were reconstituted separately with water as described above to a final concentration of 75 μg/0.1 ml and 15 IU/0.1 ml, respectively. First r-lys-plg (0.1 ml) and then r-UK (0.1 ml) was injected into the midvitreous cavity of 10 eyes using separate syringes.

R-lys-plg and r-UK were reconstituted at 75 μg/0.1 ml and 15 milliunits/0.1 ml, respectively, and mixed in Tris-HCl buffer for the preparation of the r-lys-plg and r-UK mixture. 0.2 ml of this solution was injected into the mid-vitreous cavity in 10 eyes after 20 minutes of incubation at 25° C.

Control samples were prepared for comparison with the test samples. The plasmin concentration of vitreous was measured at 10 minutes in two eyes after injection of 75 μg of r-lys-plg and in other two eyes after injection of 15 IU of urokinase. In addition to these four eyes, the color generation of normal vitreous obtained from two normal rabbit eyes was monitored.

The plasmin activity in the vitreous was determined by removing a sample from the vitreous. Vitreous aspiration was performed following the injection of r-lys-plg and r-UK at 5, 10, 30, 60, and 120 minutes. The samples were centrifuged and 100 μl of vitreous was diluted in 885 μl of lysine-phosphate buffer (0.1 M phosphate buffer, 0.07 M lysine, pH 7.5). The color generation of this solution was monitored as described above after the addition of 15 μl of S-2251 (final concentration, 0.6 mM).

These in vitro studies demonstrate that neither r-lys-plg nor r-UK alone had the ability to cleave S-2251 in Tris-HCl buffer, indicating that neither of these materials contained residual plasmin activity. Spectroscopic experiments demonstrated the activity of the reagents: S-2251 vs. purified human plasmin, r-lys-plg vs. human urokinase, and r-UK vs. purified human plasminogen. All reaction mixtures generated color and showed higher absorbance changes when the concentration of the reagent was increased. A curve similar to that of the buffer control was observed when r-lys-plg and r-UK were tested separately with S-2251 in Tris-HCl buffer.

The color generation of r-lys-plg and r-UK mixture was found to have a maximum concentration between 15 and 60 minutes. The reagents were incubated for 20 minutes to increase the rate of plasmin production. When the r-UK concentration was increased from 10 IU/ml to 100 IU/ml (in Tris-HCl buffer containing 50 μg/ml of r-lys-plg), the initial velocity of activation of r-lys-plg did not show a significant increase. Therefore, the preferred concentration for r-UK was determined to be 10 IU/ml. Because the rabbit vitreous has a volume of approximately 1.5 ml, 15 IU/ml of r-UK was injected.

Plasmin concentration of the rabbit vitreous was also determined. Although the plasmin concentrations were calculated using the plasmin standard curve and its formula, the absolute concentrations of plasmin were also determined based on its ability to generate a color gradient with S-2251 and were found to be comparable to those determined using the plasmin standard curve. Given that the plasmin activity assays using vitreous samples demonstrated a linear curve, plasmin concentration of vitreous was calculated as the slope of a plot of absorbance vs. reaction time.

Plasmin concentration of rabbit vitreous after separate intravitreal administration of r-lys-plg and r-UK was then determined. Rabbit eyes were injected intravitreally with 75 μg/0.1 ml of r-lys-plg followed by 15 IU/0.1 ml of r-UK using separate syringes. The highest plasmin concentration of vitreous, which was 351 milliunits/ml, was observed 10 minutes after separate injection of r-lys-plg and r-UK. The plasmin concentration increased between 5 and 10 minutes, and then gradually decreased after 10 minutes over a period of 2 hours.

Plasmin concentration in the rabbit vitreous after intravitreal administration of a r-lys-plg and r-UK mixture was determined. Rabbit eyes were injected intravitreally with a mixture of 75 μg/0.1 ml of r-lys-plg and 15 IU/0.1 ml of r-UK. A similar plasmin concentration curve was determined after administration of r-lys-plg and r-UK mixture except that the vitreous plasmin levels in this group were approximately one-third of that of the group that received separate administration. The highest-plasmin concentration of the vitreous in this group was 103 milliunits/ml of vitreous.

The plasmin concentrations in the vitreous of the eyes that were injected with r-lys-plg alone and r-UK alone were 1.43 and 0.57 milliunits/ml of vitreous, respectively. These values were very low when compared to those of the experimental groups and similar to the mean values (0.46 milliunits/ml of vitreous) obtained from normal rabbit eyes that had not received any injections.

Example 2

This example evaluates the safety of the compounds in the vitreous and determines the toxicity levels in the eye. Twenty eyes of 20 rabbits were used to determine the safety and toxicity of r-lys-plg and r-UK. Animals were randomly divided into 10 groups (Table 2); 2 rabbits in each group were injected with varying concentrations of r-lys-plg (10 μg/0.1 ml to 6 mg/0.1 ml) in the right eyes and 0.1 ml of balanced salt solution (BSS) in the left eyes. Ten rabbits were randomly divided into 5 groups depending on the concentration of r-UK (Table 2). Two animals in each group were injected with varying concentrations of r-UK (10 to 200 IU/0.1 ml) in the right eyes and 0.1 ml of BSS in the left eyes.

At concentrations up to 10 μg of r-lys-plg, no toxicity finding was observed upon clinical examination, ERG, and histopathology. A slight haze in the posterior vitreous was observed in all eyes at the 24-hour examination. The haze resolved over the following days without any complications. At concentrations of r-lys-plg of 250 μg and higher, all eyes demonstrated retinal vascular constriction and hemorrhages on funduscopy.

Diminished ERG responses were observed in eyes that received r-lys-plg concentrations of 1 mg or more. At concentrations of 250 and 500 μg R-lys-plg, ERGs revealed reduced amplitudes on the third day. The amplitudes returned to normal levels during the following two weeks.

Histopathologic examination demonstrated retinal vascular occlusion and red blood cell extravasation from retinal blood vessels over medullary rays.

No toxicity finding was observed with injections of r-UK at concentrations of 200 IU or lower.

No toxicity was observed in any of the eight groups after separate intravitreal administration of r-lys-plg and r-UK. A slight temporary haze in the posterior vitreous was observed in every eye that was injected with r-lys-plg.

$SF_6$ gas expanded and filled 40% to 60% of the vitreous cavity upon examination at 24 hours in all 12 eyes that received gas injection. No complications of gas injection were observed; the gas was completely resorbed approximately 7 days after its injection.

Example 3

This example measures the efficacy of the compounds in the formation of posterior vitreous detachment. The test data are reproduced in Table 1.

Twenty-two animals were divided into eight groups (2–4 rabbits per group). The right eye of each rabbit was injected with either BSS (Groups 1, 5), r-lys-plg (Groups 2, 6), r-UK (Groups 3, 7), or 75 μg r-lys-plg and r-UK (Groups 4, 8). Two hours after the first set of injections, 0.4 ml of 100% $SF_6$ was injected in half of the eyes that previously received the injection of BSS (Group 5), r-lys-plg (Group 6), r-UK (Group 7), and a combination of r-lys-plg and r-UK (Group 8). $SF_6$ injection was performed under direct visualization with an indirect ophthalmoscope through a 30-gauge needle. The lower pars plana was used for gas injection and the animal's head was kept in a vertical position following injection to prevent gas escape from the injection site. Anterior chamber paracentesis was performed before gas injection to prevent acute pressure rise.

Rabbits in all eight groups were followed biweekly with slit-lamp biomicroscopy, binocular indirect ophthalmoscopy, and tonometry. A Goldmann contact lens was used for evaluation of the vitreous body and vitreoretinal juncture. Electroretinograms (ERG) were recorded with the UTAS-E 2000 system (LKC Technologies, Inc. Gaithersburg, Md.) before and then 3, 7, and 14 days after intravitreal injections. The pupils were dilated for ERG recordings and the rabbits were anaesthetized and dark adapted for 30 minutes. Topical anesthetic drops were then applied and ERG-Jet disposable contact lens electrodes were placed over the cornea. After the positioning of reference and ground electrodes, dark-adapted and light-adapted ERGs were recorded simultaneously from both eyes. Five responses were averaged for each step of the ERG. B-wave amplitudes of preinjection and postinjection ERGs were compared and a decease of more than 30% in the b-wave amplitude was considered significant.

All animals were sacrificed at two weeks. All eyes were enucleated under deep anesthesia immediately before the animals were euthanized by carbon dioxide inhalation.

The globes were penetrated and then fixed in Karnovsky fixative (pH 7.2) overnight. After 24 hours, the fixated eyes were bisected horizontally over the optic nerve into superior and inferior calottes in a circumferential manner to keep the lens in its place. The vitreoretinal attachment was assessed with inverted and suspended-in-air calotte technique. Gross specimens were photographed using a digital color video camera (DXC-390, Sony Electronics Inc., Park Ridge, N.J.) attached to a slit-lamp biomicroscope (Haag-Streit, Bern, Switzerland).

For light microscopy, the tissue was transferred into phosphate buffer saline and kept at 4° C. overnight. After dehydration through a graded ethanol series, the specimen was preinfiltrated and infiltrated with Technovit 7100 (Energy Beam Sciences Inc., Agawam, Wash.) and embedded in glycol methacrylate. Three-micron sections were stained with 1% toluidine blue and examined under the microscope.

For scanning electron microscopy (SEM), after 24 hours of initial fixation, selected specimens were rinsed with phosphate buffer solution, postfixed in 1% osmium tetroxide, dehydrated in hexamethyldisilazane (HMDS) and sputter coated in gold. The JSM-820 scanning electron microscope (JEOL USA Inc. Peabody, Mass.) was used for further evaluation of the vitreoretinal juncture. With the exception of one eye from Group 1, eyes without any sign of vitreoretinal separation were not evaluated with SEM.

TABLE 1

Experimental Groups of Rabbits Injected with Recombinant Lysine Plasminogen, Recombinant Urokinase, Sulfur Hexafluoride, and Balanced Saline Solution

| Groups | Intravitreal injection | Number of eyes | Concentration (in 0.1 ml) | Cavity Formation | Presence of cortical vitreous | Presence of PVD | |
|---|---|---|---|---|---|---|---|
| Group 1 | BSS | 2 | 0.2 ml | N | N | N | |
| Group 2 | r-lys-plg | 2 | 75 μg r-lys-plg | N | N | N | |
| Group 3 | r-UK | 2 | 15 IU r-UK | N | N | N | |
| Group 4 | r-lys-plg + r-UK | 4 | 75 μg r-lys-plg + 15 IU r-UK | 50% | 25% | 25% P | |
| Group 5 | BSS + $SF_6$ | 4 | 0.2 ml BSS + 0.4 ml 100% $SF_6$ | 100% | 50% | 25% P 25% C | Groups 5, 6 and 7 |
| Group 6 | r-lys-plg + $SF_6$ | 2 | 75 μg r-lys-plg + 0.4 ml 100% $SF_6$ | 100% | 50% | 50% P | combined 25% P |
| Group 7 | r-UK + $SF_6$ | 2 | 15 IU r-UK + 0.4 ml 100% $SF_6$ | 100% | 100% | — | 13% C |
| Group 8 | r-lys-plg + r-UK + $SF_6$ | 4 | 75 μg r-lys-plg + 15 IU r-UK + 0.4 ml 100% $SF_6$ | 100% | 25% | 25% P 75% C | |

All of the eyes of Group 1 injected with BSS showed no signs of cavity formation or separation of the vitreous. The eyes of Group 2 injected with r-lys-plg, Group 3 injected with r-UK also showed no signs of cavity formation or separation of the vitreous. The Group 4 eyes injected with r-lys-plg and r-UK showed that the vitreous was attached in 50% of the eyes.

On gross specimen examination, all twelve eyes that were injected with $SF_6$ (Groups 5–8) demonstrated a vitreous cavity. Fifty percent of the eyes in Group 4 also showed cavity formation. A thin layer of cortical vitreous remained attached to the retinal surface and accompanied cavity formation in all eyes in Group 7 (injected with r-UK and $SF_6$), in 50% of the eyes in Groups 5 and 6 (injected with BSS and $SF_6$, and r-lys-plg and $SF_6$, respectively) and in 25% of the eyes in Groups 4 and 8 (injected with r-lys-plg and r-UK, and r-lys-plg, r-UK, and $SF_6$, respectively). These eyes demonstrated a smooth light reflex on the retinal surface. The light reflex was rough if the cortical vitreous was not detected on the retina. In one eye each in Groups 5 and 8, a transvitreal band extended between the optic nerve and the posterior lens surface.

The vitreous was completely detached from the posterior retinal surface in 75% of the eyes in Group 8, and in 25% of the eyes in Group 5. Fifty percent of the eyes in Group 6 and 25% of the eyes in Groups 4, 5, and 8 showed a small area of PVD, which was no larger than one-quarter of the calotte.

The eyes in Group 8 were compared with all the other eyes that received $SF_6$ injection (Groups 5, 6, and 7, combined). The PVD rate in Group 8 was 75% for complete PVD and 25% partial PVD. The PVD rates in other groups (Groups 5, 6, and 7 combined) were 13% complete PVD and 25% partial PVD.

In all eyes, the vitreous was attached to the retina at the vitreous base. Examination by scanning electron microscopy (SEM) of one eye in Group 1 (BSS only) revealed that the retinal surface was completely covered with a dense meshwork of collagen fibers. In Group 4 (r-lys-plg and r-UK), a loose distribution of collagen fibers was noted. Bare ILM was also appreciated in some small parts, albeit rarely.

The eyes in Group 5 (BSS, $SF_6$) demonstrated a smooth undulated surface of the bare internal limiting membrane (ILM) in some parts of the specimen. In other parts of the specimen, compressed collagen fibers were observed. In Group 8 (r-lys-plg, r-UK, and $SF_6$), a smooth surface of ILM was observed throughout the specimen except for small islands that contained some collagen fibers located close to the retinal vessels.

Example 4

This example evaluates the toxicity levels of plasminogen, urokinase and a combination of urokinase and plasminogen in the eye. The toxicity of the components was determined by introducing the component into the eye of albino rabbits and determining the effects as observed by electroretinogram. The dosage of the component and the time of the detected toxicity are presented in the Table I below. The toxicity was determined by the occurrence of inflammation of the retina and the blood vessels and arteries in the choroid and retina.

TABLE I

| Plasminogen dose | Toxicity | Action |
| --- | --- | --- |
| 2 µg | Non-toxic | – |
| 5 µg | Non-toxic | – |
| 10 µg | Non-toxic | – |
| 20 µg | Vasculitis clinically (completely regressed after 7 days Normal ERG) | + After 24 hours |
| 50 µg | Vasculitis clinically Normal ERG | + After 8 hours |
| 100 µg | Vasculitis clinically Normal ERG | + After 8 hours |

TABLE I-continued

| Plasminogen dose | Toxicity | Action |
| --- | --- | --- |
| 200 µg | Toxic | + After 8 hours |
| 500 µg | Toxic | + After 8 hours |
| 1000 µg | Toxic | + After 8 hours |
| 2000 µg | Toxic | + After 8 hours |
| 5000 µg | Toxic | + After 8 hours |
| 10000 µg | Toxic | + After 4 hours |
| Urokinase | | |
| 200 µg | Non-toxic clinically | – |
| 500 µg | Non-toxic clinically | – |
| Urokinase 200 µg + Plasminogen | | |
| 2 µg | Non-toxic clinically | – |
| 5 µg | Non-toxic clinically | – |
| 10 µg | Non-toxic clinically | + After 6 hours |
| 15 µg | Non-toxic clinically | + After 6 hours |

Example 5

A second group of albino rabbits was tested to evaluate the toxicity levels of plasminogen and urokinase in the eye. The toxicity of the components was determined by introducing the component into the eye of the rabbits and determining whether any inflammation occurred as observed by electroretinogram. The dosage of the component and the detected toxicity are presented in Table II. The toxicity was determined by the occurrence of inflammation of the retina and the blood vessels and arteries in the choroid and retina.

TABLE II

| Plasminogen dose | Toxicity | Action |
| --- | --- | --- |
| 20 µg | Non-toxic | – |
| 20 µg Urokinase | Non-toxic | – |
| 1000 IU | Non-toxic | – |
| Urokinase 500 IU + Plasminogen | | |
| 10 µg | Non-toxic | – |
| 10 µg | Non-toxic | – |
| 15 µg | Non-toxic | + After 24 hours |
| 15 µg | Non-toxic | + After 1½ hours |
| 20 µg | Non-toxic | + After 1½ hours |
| 20 µg | Non-toxic ERG changes on Step 1 | + After 1½ hours |

Example 6

Test samples were prepared to compare the effects of plasminogen alone, urokinase alone and a combination of plasminogen and urokinase on the eye. A stock solution of low molecular weight, purified recombinant urokinase was obtained from Abbott Laboratories, North Chicago, Ill. having a concentration of 407,000 IU/ml. This solution was diluted with balanced salt solution to produce solutions having 10,000 IU/ml, 5,000 IU/ml, and 1,000 IU/ml.

Purified human plasminogen was obtained having a concentration of 220 caseinolytic units (CU) per milliliter. The plasminogen was diluted in balanced salt solution to form solutions having the concentrations set forth in Table 1. Additional samples solutions were prepared containing 1,000 IU urokinase and concentrations of plasminogen ranging from 0.1 to 2.0 units as set forth in Table 1.

Albino New Zealand rabbits weighing approximately 2 Kg were used in this example and were treated according to ARVO resolution for use of animals in research. A detailed ophthalmologic examination was performed on the rabbits with indirect ophthalmoscope and slit lamp biomicroscopy using a 60-diopter lens. Only normal rabbits were used in this experiment.

The rabbits were divided into three groups and anesthetized using 50 mg/kg Ketamine and 5 mg/kg xylazine. The conjunctiva were sterilized with 5% povidone iodine and rinsed with a balanced salt solution. Anterior chamber paracentesis was performed just prior to injection to prevent hypertension.

The right eye of each rabbit was injected with samples of Table 1 using a tuberculin syringe fitted with a 30-gauge needle. The samples were injected 3 mm posterior to the limbus into the midvitreous cavity under direct observation. The Group I rabbits were injected intravitreally with pure urokinase at a dose of 1,000 IU, 5,000 IU and 10,000 IU. The Group II rabbits were injected intravitreally with recombinant plasminogen at a dose of 0.1, 0.4, 1.0, 2.0, 4.0, 8.0, 16.0 caseinolytic units (CU). The Group III rabbits were injected intravitreally with a combination of 1,000 IU urokinase and nontoxic concentrations of 0.1, 0.4, 1.0, 2.0 units of plasminogen. The left eyes were injected with a balanced salt solution as control samples.

Electrophysiology

Electroretinography (ERG) recordings were performed before injection and then repeated 3 days and 15 days after injection. The rabbits were anesthetized and kept for 30 minutes in a dark room before ERG recordings. The UTAS-E 2000 system (LKC Technologies, Gaithersburg, Md.) was used for the ERG. The conjunctive and cornea were anesthetized with proparacaine 0.5%. Unipolar contact lenses were placed on both corneas with methylcellulose. The negative electrode was placed into the subcutaneous space of the forehead and the ground electrode was clipped to the earlobe with electric gel. Both dark adapted and light adapted stimulus were recorded. The average of three sweeps was taken for each step. B-wave amplitude after injection was compared to the preinjection value of the same eye. A decrease in b-wave amplitude of greater than 30% was considered significant.

Follow Up

The eyes were evaluated by slit lamp examination and indirect fundus ophthalmoscopy immediately after injection to detect any ocular trauma caused by the injection. Detailed ophthalmologic examinations were done 30 minutes, 1, 2, 8, 12, and 24 hours and 3, 10, and 15 days after injection. Fundus photographs were taken at different times. B-mode ultrasonography (Innovative Imaging Inc. System, Sacramento, Calif.) was performed to reveal PVD.

Histology

The rabbits were sacrificed with an intravenous injection of sodium pentobarbital (100 mg/kg) 2 weeks after injection with the test samples. The eyes were enucleated and penetrated 2.5 mm posterior to the limbus to allow the fixative solution to fill the eyes rapidly. Eyes were fixed in 2% paraformaldehyde and 3% glutaraldehyde. After 24 hours of fixation, a hemidissection of the globe was performed at roughly the horizontal meridian using a thin, sharp blade. The incision was completed, dividing the globe into superior and inferior pieces which were inspected to ensure that the vitreous had been cut completely. Each piece of the globe was tilted, anterior segment down, and the vitreoretinal attachment was evaluated as described by Foos. If a total posterior vitreous detachment had occurred, the vitreous fell away from the retinal surface by gravity. If there was no posterior vitreous detachment or only partial separation, the vitreous was suspended from the eye cup.

Paraffin sections were stained with hematoxylin and eosin for evaluation of retinal toxicity and vitreoretinal interface features under a light microscope. Small pieces of retina, close to the optic nerve, were taken from both experimental and control eyes. The specimens were processed for transmission electron microscopy (TEM). Thin sections were stained with uranyl acetate and lead citrate and observed under a transmission electron microscope (EMTO C/Cr; Zeiss, Oberkochen, Germany). Special attention was paid to the inner limiting membrane (ILM) and collagen fiber attachment to the ILM.

The effects of the various samples on the eye are set forth in Table III. The eyes injected with Samples 1 and 2 (10,000 IU and 5,000 IU urokinase) showed whitish-gray retinal lesions inferior to the optic disc in the posterior pole. Some minor retinal hemorrhage and dense vitreous inflammation were noticed in the eyes of Samples 1 and 2. Sample 3 containing 1,000 IU urokinase showed no vitreous haze, hemorrhage, inflammation, cataract or other complications.

The Group II Samples 4 and 5 containing 16 CU and 8 CU of plasminogen caused moderate to severe intraocular inflammation. Sample 6 containing 4.0 CU of plasminogen resulted in a very limited amount of inflammation of the vitreous. Samples 7–10 containing 2.0 CU, 1.0 CU, 0.4 CU and 0.1 CU, respectively, showed no vitreous haze, hemorrhage inflammation or cataract.

The Group III Samples 11–14 containing 1,000 IU urokinase and 2.0 CU, 1.0 CU, 0.4 CU and 0.1 CU, respectively, showed no vitreous haze, hemorrhage, inflammation or cataract. In Samples 11–14, posterior vitreous detachment was detected ophthalmoscopically for the first time about 8 hours after injection. At 12 hours, all eyes of Samples 11 and 12 containing 2.0 CU and 1.0 CU plasminogen and 1000 IU urokinase showed complete posterior vitreous detachment which was confirmed with ultrasonography. Sample 13 containing 0.4 CU plasminogen and 1000 IU urokinase resulted in three eyes with total posterior vitreous detachment and one with partial posterior vitreous detachment. Sample 14 containing 0.1 CU plasminogen and 1000 IU urokinase resulted in an eye with total posterior vitreous detachment and three eyes partial posterior detachment. All of the control eyes showed no posterior vitreous detachment.

Gross examination of enucleated eyes showed similar results to the results of the fundus examination. The vitreous fell away from the retina in all of the eyes of Samples 11 and 12. Three eyes of Sample 13 and one eye of Sample 14 showed total vitreous separation while the others showed partial separation.

Electrophysiology

ERG recordings demonstrated that doses of 5,000 to 10,000 IU of Samples 1 and 2 were toxic to the retina. The b-wave amplitudes in more than 60% in both doses when compared the preinjection value. The ERG results were normal for all eyes of Samples 4–10 of Group II and Samples 11–14 of Group III although the eyes of Samples 4–6 showed inflammation.

Light Microscopy

Histologic sections of eyes of Samples 1 and 2 containing 10,000 IU and 5,000 IU urokinase showed intensive disorganization of the retina. The eyes of sample 3 containing 1,000 IU urokinase showed normal retinal structure.

In Group II Samples 4–6, respectively showed minimal, moderate and severe intraocular inflammatory cell response in the vitreous. Samples 7–10 were normal. However, no posterior vitreous detachment was observed. Control eyes were normal and showed no posterior vitreous detachment.

The Samples 11–14 of Group III showed separation of the vitreoretinal interface depending on the plasminogen concentration. Complete posterior vitreous detachment was observed in all eyes of Samples 11 and 12. Sample 13 showed complete posterior vitreous detachment in three eyes with partial detachment in the other. Sample 14 showed complete detachment in one eye and partial detachment in the remaining three.

Electron Microscopy

Group III eyes of Samples 11–14 showed empty vitreous cavities and smooth internal surfaces of the retina. No collagen fibers were seen adjacent the retinal surface. The control showed persistent vitreous collagen fibers attached to the retinal surface.

TABLE III

| | Drug Dose | | | | No. of Total | No. of Partial | |
|---|---|---|---|---|---|---|---|
| | Urokinase | Plasminogen | Vol. | No. of Eyes | PVD | PVD | Inflammation |
| Group I | | | | | | | |
| Sample 1 | 10,000 IU | — | 0.1 ml | 4 | 0 | 0 | yes |
| Sample 2 | 5,000 IU | — | 0.1 ml | 4 | 0 | 0 | yes |
| Sample 3 | 1,000 IU | — | 0.1 ml | 4 | 0 | 0 | no |
| Group II | | | | | | | |
| Sample 4 | — | 16.0 CU | 0.1 ml | 4 | 0 | 0 | yes |
| Sample 5 | — | 8.0 CU | 0.1 ml | 4 | 0 | 0 | yes |
| Sample 6 | — | 4.0 CU | 0.1 ml | 4 | 0 | 0 | yes |
| Sample 7 | — | 2.0 CU | 0.1 ml | 4 | 0 | 0 | no |
| Sample 8 | — | 1.0 CU | 0.1 ml | 4 | 0 | 0 | no |
| Sample 9 | — | 0.4 CU | 0.1 ml | 4 | 0 | 4 | no |
| Sample 10 | — | 0.1 CU | 0.1 ml | 4 | 0 | 4 | no |
| Group III | | | | | | | |
| Sample 11 | 1,000 IU | 2.0 CU | 0.1 ml | 4 | 4 | 0 | no |
| Sample 12 | 1,000 IU | 1.0 CU | 0.1 ml | 4 | 4 | 0 | no |
| Sample 13 | 1,000 IU | 0.4 CU | 0.1 ml | 4 | 3 | 1 | no |
| Sample 14 | 1,000 IU | 0.1 CU | 0.1 ml | 4 | 1 | 3 | no |
| Control (Balanced Salt Solution) | — | — | 0.1 ml | 56 | 0 | 0 | no |

Although the invention has been described with a certain degree of particularity, it is understood that the present disclosure has been made only by way of example and that numerous changes in the details of construction and the combination and arrangement of parts may be resorted to without departing from the spirit and scope of the invention. Thus, the scope of the invention should not be limited by the foregoing specification, but rather, only by the scope of the claims appended hereto.

What is claimed is:

1. A process for preventing or inhibiting retinal hemorrhaging, retinal tears and retinal detachment in the eye of a patient caused by vitreous traction, said process comprising the steps of:

introducing recombinant lysine-plasminogen, recombinant plasminogen activator and a gaseous adjuvant material into the vitreous of the eye of a patient in need thereof in an amount effective to produce plasmin in the vitreous to induce substantially complete separation of posterior hyaloid from the inner limiting membrane in said eye, without removing the vitreous from said eye, thereby inhibiting retinal hemorrhaging, retinal tears, and retinal detachment, wherein each of said components of said composition are introduced into the eye in a non-toxic amount substantially without inflammation and where said gaseous material is introduced into the vitreous in an amount sufficient to compress said vitreous against said retina while said composition induces posterior vitreous detachment.

2. The process of claim 1, wherein said gaseous adjuvant material is introduced simultaneously with said recombinant lysine-plasminogen and recombinant plasminogen activator into said vitreous.

3. The process of claim 1, wherein said gaseous adjuvant material is introduced after introducing said lysine-plasminogen and recombinant plasminogen activator.

4. The process of claim 2, wherein said gaseous adjuvant material is selected from the group consisting of a perfluorocarbon, nitrogen, air, oxygen, carbon dioxide, argon and sulfur hexafluoride.

5. The process of claim 1, wherein said plasminogen activator selected from the group consisting of recombinant urokinase, recombinant streptokinase and recombinant tissue plasminogen activator.

6. The process of claim 1, wherein said plasminogen activator is recombinant urokinase, and where said process comprises introducing glucose in a balanced saline solution into said vitreous to crosslink collagen in said vitreous.

7. The process of claim 1, comprising injecting said recombinant lysine-plasminogen into the vitreous of said eye at a dose of about 500 IU to about 1000 IU.

8. The process of claim 1, further comprising injecting a collagen crosslinking agent in an amount of about 3 wt % to about 6 wt %.

9. The process of claim 1, comprising introducing said recombinant lysine-plasminogen in a pharmaceutically acceptable carrier at a concentration of about 50 µg/0.1 ml to about 200 µg/0.1 ml.

10. The process of claim 9, wherein said recombinant lysine-plasminogen is introduced at a concentration of about 100 µg/0.1 ml or less.

11. The process of claim 1, wherein said plasminogen activator is recombinant urokinase and said process comprises injecting said recombinant urokinase at a dose of about 200 IU or less.

12. The process of claim 1, wherein said plasminogen activator is recombinant urokinase and said process comprises introducing said recombinant lysine-plasminogen at a dose of about 1000 IU or less, and introducing said recombinant urokinase at a dose of about 200 IU.

13. The process of claim 1, comprising introducing said gaseous adjuvant material into said vitreous in an amount to form a cavity of about 40% to about 60% by volume of said eye.

14. The process of claim 8, wherein said collagen crosslinking agent is selected from the group consisting of transglutaminase and a reducing sugar.

15. The process of claim 8, wherein said collagen crosslinking agent is selected from the group consisting of fructose, glucose, glycerose, threose, erythose, lyxose, xylose, arabinose, ribose, allose, altrose, mannose, gulose, idose, galactose, and talose.

16. A process for inducing substantially complete posterior vitreous detachment in the eye of a patient comprising the steps of:
    introducing recombinant lysine-plasminogen in a pharmaceutically acceptable carrier at a concentration of about 200 µg/0.1 ml or less into the vitreous of the eye of a patient in need thereof,
    introducing recombinant urokinase in a pharmaceutically acceptable carrier at a dose of about 200 IU or less, and
    thereafter introducing an expanding gaseous adjuvant into the vitreous, said recombinant lysine-plasminogen, recombinant urokinase, and gaseous adjuvant being introduced into said vitreous in an amount to induce substantially complete separation of posterior hyaloid from the inner limiting membrane in said eye to form a vitreoretinal surface substantially devoid of vitreous collagen without removing said vitreous from said eye, wherein each of said components of said composition are introduced into the eye in a non-toxic amount substantially without inflammation and without removing said vitreous from the eye.

17. The process of claim 16, comprising injecting said recombinant lysine-plasminogen into the vitreous of said eye at a dose of about 1000 IU or less.

18. The process of claim 16, further comprising introducing a transglutaminase collagen crosslinking agent.

19. The process of claim 16, further comprising introducing a reducing sugar as a collagen crosslinking agent.

20. The process of claim 16, further comprising introducing a collagen crosslinking agent selected from the group consisting of fructose, glucose, glycerose, threose, erythose, lyxose, xylose, arabinose, ribose, allose, altrose, mannose, gulose, idose, galactose, and talose.

21. The process of claim 16, further comprising the step of introducing said gaseous adjuvant into the vitreous in an amount of about 0.3 ml to about 1.0 ml to compress said vitreous against said retina.

22. The process of claim 16, wherein said gaseous adjuvant is selected from the group consisting of perfluorocarbon gas, air, carbon dioxide, nitrogen, argon and mixtures thereof.

23. The process of claim 22, wherein said gaseous adjuvant is selected from the group consisting of sulfurhexafluoride ($SF_6$), air, and mixtures thereof.

24. A process for inducing substantially complete posterior vitreous detachment in the eye of a patient in need thereof to prevent or inhibit retinal tears and retinal detachment, comprising the step of:
    introducing lysine-plasminogen into the vitreous of the eye of a patient in need thereof, introducing a recombinant plasminogen activator into said vitreous, and introducing a gaseous adjuvant material and a collagen crosslinking agent into said vitreous, said lysine-plasminogen, recombinant plasminogen activator, and gaseous adjuvant material being introduced into said vitreous in an amount to induce substantial separation of posterior hyaloid from the inner limiting membrane in said eye where a vitreo-retinal surface is substantially devoid of vitreous collagen to prevent or inhibit retinal hemorrhaging, retinal tears and retinal detachment, wherein each of said components of said composition are introduced into the eye in a non-toxic amount substantially without inflammation.

25. The process of claim 24, wherein said recombinant plasminogen activator is urokinase and said process comprises injecting said urokinase at a dose of about 200 IU or less.

26. The process of claim 25, wherein process comprises introducing said lysine-plasminogen at a dose of about 1000 IU or less.

27. The process of claim 24, wherein said recombinant lysine-plasminogen is introduced into said vitreous in a pharmaceutically acceptable carrier at a concentration of about 200 µg/0.1 ml or less.

28. The process of claim 24, wherein said recombinant lysine-plasminogen is introduced in a pharmaceutically acceptable carrier at a concentration of about 100 µg/0.1 ml or less.

29. The process of claim 24, wherein said collagen crosslinking agent is selected from the group consisting of fructose, glucose, glycerose, threose, erythose, lyxose, xylose, arabinose, ribose, allose, altrose, mannose, gulose, idose, galactose, and talose.

30. The process of claim 29, wherein said collagen crosslinking agent is introduced as a 5 wt % glucose solution.

31. The process of claim 24, wherein said gaseous adjuvant material is introduced in an amount sufficient to compress said vitreous against the retina of said eye and to form a cavity.

32. The process of claim 31, wherein said gaseous material is introduced into said vitreous after introducing said recombinant lysine-plasminogen and recombinant plasminogen activator into said vitreous.

33. The process of claim 31, wherein said gaseous material is selected from the group consisting of perfluorocarbon, air, oxygen, nitrogen, carbon dioxide, argon, and mixtures thereof.

34. The process of claim 31, wherein said gaseous material is selected from the group consisting of sulfurhexafluoride, air, and mixtures thereof.

35. The process of claim 31, comprising introducing said gaseous material into the eye in an amount of about 0.3 ml to about 1.0 ml.

36. The process of claim 24, comprising introducing said gaseous adjuvant into said vitreous in an amount to form a cavity filling about 40% to about 60% of internal volume of said eye.

37. A process for preventing or inhibiting retinal hemorrhaging, retinal tears and retinal detachment in the eye of a patient caused by vitreous traction without removing the vitreous from said eye, said process comprising the steps of:

introducing plasminogen and a plasminogen activator into the vitreous of the eye of a patient at risk of vitreous traction in an amount effective to produce plasmin in the vitreous to induce substantially complete separation of posterior hyaloid from the inner limiting membrane in said eye, thereby inhibiting retinal hemorrhaging, retinal tears, and retinal detachment, wherein each of said components of said composition are introduced into the eye in a non-toxic amount substantially without inflammation and without removing said vitreous from said eye.

38. The process of claim 37, wherein said plasminogen is recombinant lysine-plasminogen and wherein said plasminogen activator is a recombinant plasminogen activator.

39. The process of claim 37, wherein said process further comprises introducing a gaseous material into the vitreous in an amount sufficient to compress said vitreous against said retina while said composition induces posterior vitreous detachment.

40. The process of claim 39, wherein said gaseous material is introduced simultaneously or after introducing said plasminogen and plasminogen activator.

* * * * *